United States Patent

Limon et al.

[11] Patent Number: 6,027,526
[45] Date of Patent: Feb. 22, 2000

[54] STENT HAVING VARIED AMOUNTS OF STRUCTURAL STRENGTH ALONG ITS LENGTH

[75] Inventors: Timothy A. Limon, Cupertino; Todd H. Turnlund, Sunnyvale, both of Calif.

[73] Assignee: Advanced Cardiovascular Systems, Inc., Santa Clara, Calif.

[21] Appl. No.: 08/943,992

[22] Filed: Oct. 3, 1997

Related U.S. Application Data

[63] Continuation of application No. 08/630,787, Apr. 10, 1996, abandoned.

[51] Int. Cl.$^7$ ...................................................... A61F 2/06
[52] U.S. Cl. ................................ 623/1; 623/12; 606/198; 606/194
[58] Field of Search .................................... 623/1, 11, 12, 623/66; 606/108, 191–195, 198

[56] References Cited

U.S. PATENT DOCUMENTS

| | | | |
|---|---|---|---|
| 4,241,146 | 12/1980 | Sivachenko et al. | 428/600 |
| 4,725,334 | 2/1988 | Brimm | 428/600 |
| 4,728,328 | 3/1988 | Hughes et al. | 623/12 |
| 4,830,003 | 5/1989 | Wolff et al. | 623/1 |
| 4,986,831 | 1/1991 | King et al. . | |
| 5,019,090 | 5/1991 | Pinchuk | 623/1 |
| 5,064,435 | 11/1991 | Porter . | |
| 5,108,417 | 4/1992 | Sawyer . | |
| 5,133,732 | 7/1992 | Wiktor | 623/1 |
| 5,135,536 | 8/1992 | Hillstead | 623/1 |
| 5,195,984 | 3/1993 | Schatz | 623/1 |
| 5,344,425 | 9/1994 | Sawyer . | |
| 5,354,308 | 10/1994 | Simon et al. | 623/1 |
| 5,366,504 | 11/1994 | Andersen et al. | 623/1 |
| 5,383,892 | 1/1995 | Cardon et al. | 623/1 |
| 5,395,390 | 3/1995 | Simon et al. . | |
| 5,413,597 | 5/1995 | Krajicek . | |
| 5,421,955 | 6/1995 | Lau et al. | 216/48 |
| 5,449,373 | 9/1995 | Pinchasik et al. | 623/1 |
| 5,476,506 | 12/1995 | Lunn . | |
| 5,514,154 | 5/1996 | Lau et al. | 606/194 |
| 5,527,324 | 6/1996 | Krantz et al. | 623/12 |
| 5,569,295 | 10/1996 | Lam | 623/1 |
| 5,601,593 | 2/1997 | Freitag | 623/12 |
| 5,630,829 | 5/1997 | Lauterjung | 623/1 |
| 5,636,641 | 6/1997 | Fariabi | 623/1 |
| 5,693,089 | 12/1997 | Inoue | 606/108 |
| 5,707,388 | 1/1998 | Lauterjung | 623/1 |
| 5,716,393 | 2/1998 | Linderberg et al. | 623/1 |
| 5,741,327 | 4/1998 | Frantzen | 623/12 |
| 5,759,192 | 6/1998 | Saunders | 606/194 |
| 5,776,161 | 7/1998 | Globerman | 606/194 |
| 5,810,868 | 9/1998 | Lashinski et al. | 606/194 |
| 5,843,120 | 12/1998 | Israel et al. | 606/198 |
| 5,868,783 | 2/1999 | Tower | 623/1 |
| 5,913,895 | 6/1999 | Burpee et al. | 623/1 |

FOREIGN PATENT DOCUMENTS

| | | | |
|---|---|---|---|
| 0 201 466 | 11/1986 | European Pat. Off. . | |
| 0 541 443 | 5/1993 | European Pat. Off. . | |
| 540290 | 5/1993 | European Pat. Off. | 623/1 |
| 606165 | 7/1994 | European Pat. Off. | 623/1 |
| 0 688 545 | 12/1995 | European Pat. Off. . | |
| 94/17754 | 8/1994 | WIPO | 623/1 |
| WO 95 23563 | 9/1995 | WIPO . | |
| WO 95 26695 | 10/1995 | WIPO . | |
| WO 96/09013 | 3/1996 | WIPO . | |

OTHER PUBLICATIONS

Webster's II New Riverside University Dictionary, p. 373, 1994.

*Primary Examiner*—Paul B. Prebilic
*Attorney, Agent, or Firm*—Fulwider Patton Lee & Utecht, L.L.P.

[57] ABSTRACT

The invention is directed to an expandable stent for implanting in a body lumen, such as a coronary artery. The stent has an open lattice structure and is constructed so that at least one end section has a thicker cross-section and corresponding greater radial strength than the remaining sections of the stent.

2 Claims, 7 Drawing Sheets

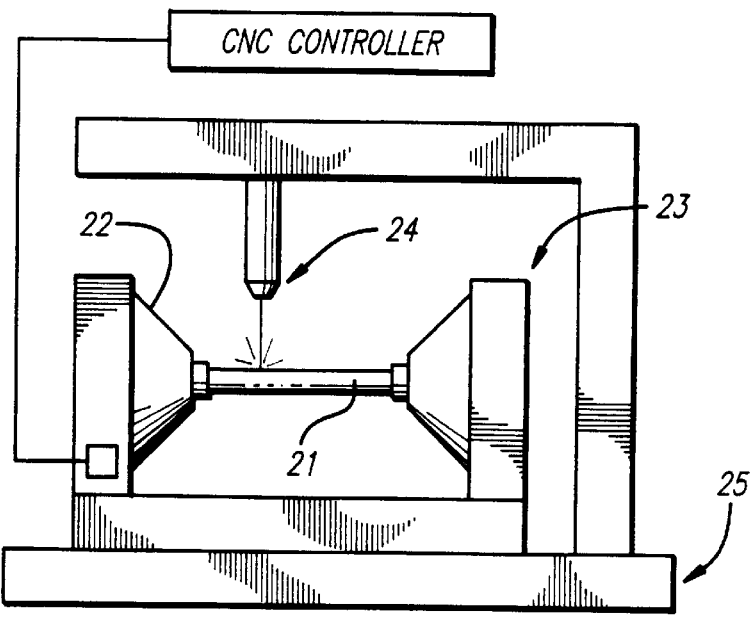
FIG. 6
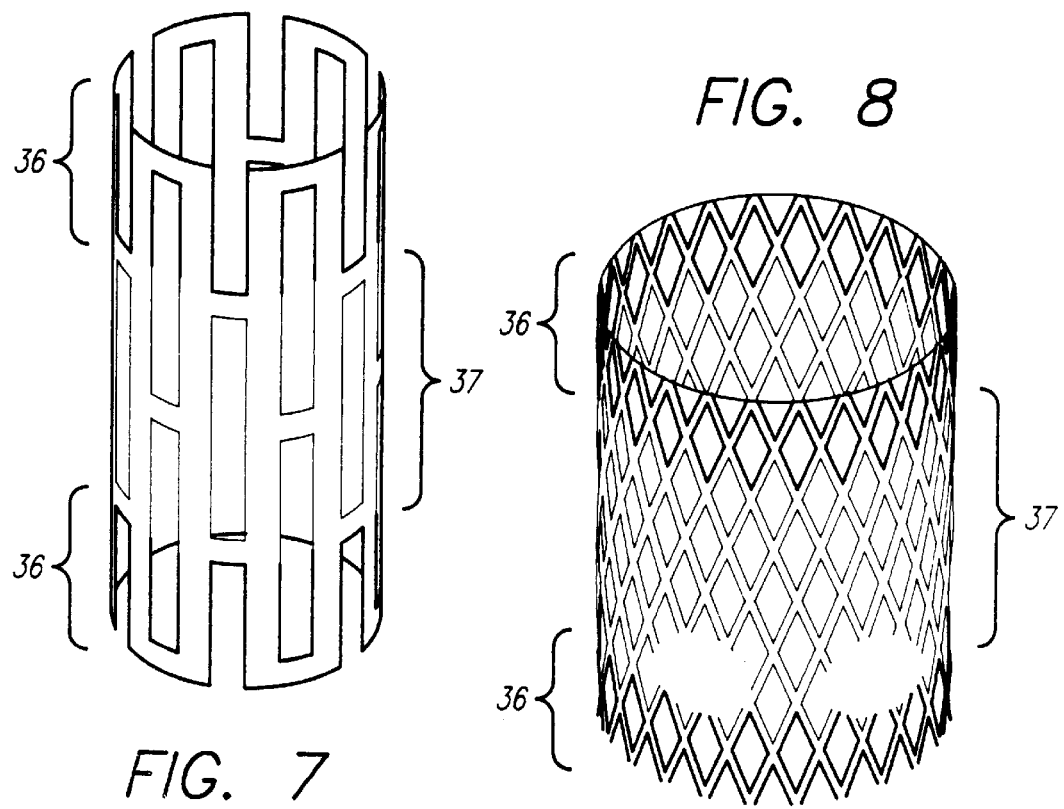
FIG. 7
FIG. 8

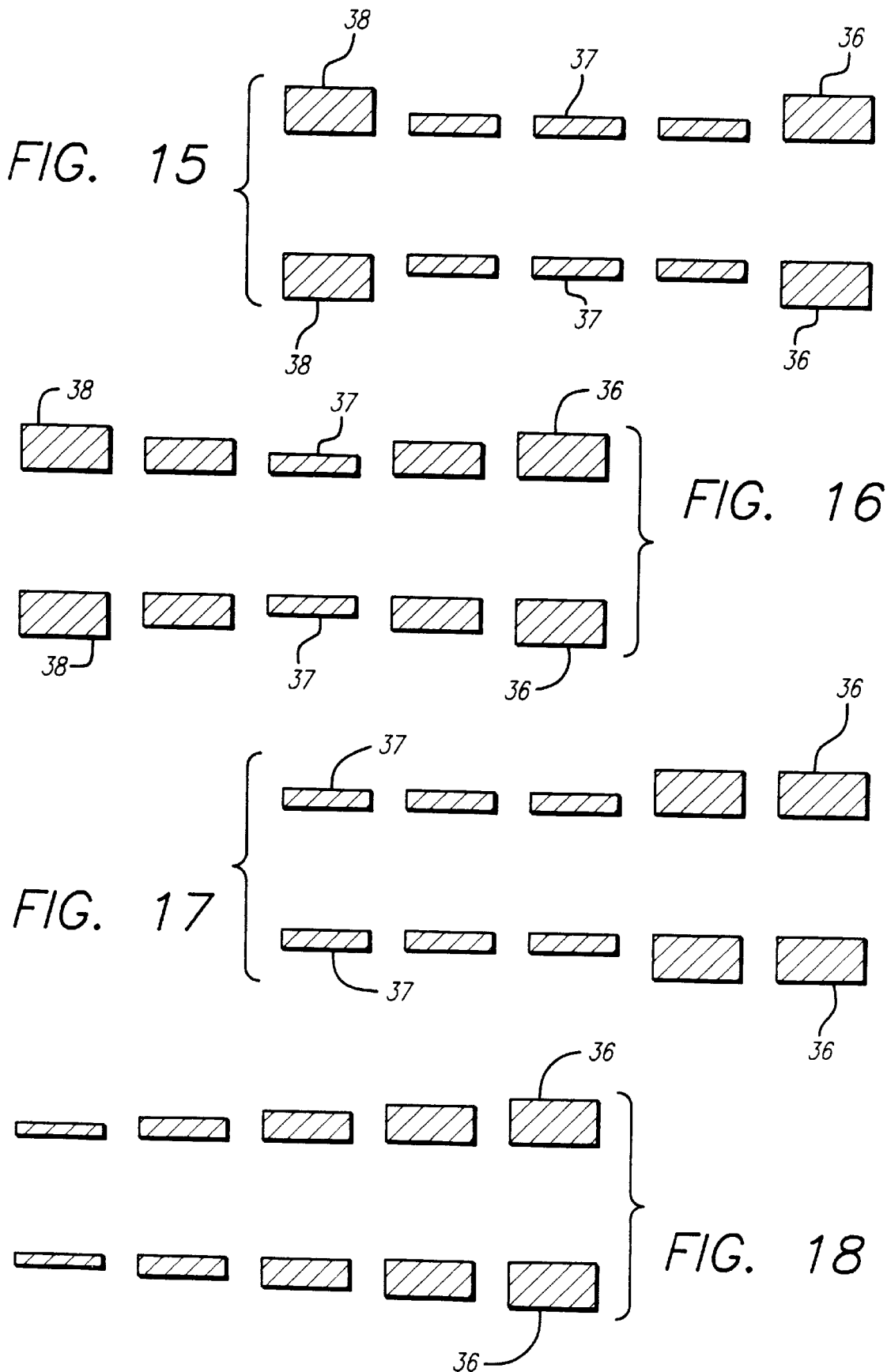

STENT HAVING VARIED AMOUNTS OF STRUCTURAL STRENGTH ALONG ITS LENGTH

This application is a continuation of application Ser. No. 08/630,787, filed on Apr. 10, 1996 now abandoned.

BACKGROUND OF THE INVENTION

FIELD OF THE INVENTION

This invention relates to expandable endoprosthesis devices, generally referred to as stents, which are adapted to be implanted into a patient's body lumen, such as blood vessel or coronary artery, to maintain the patency thereof. These devices are useful in the treatment of atherosclerotic stenosis in blood vessels.

Stents are generally tubular-shaped devices which function to hold open a segment of a blood vessel or other anatomical lumen. They are particularly suitable for use to support and hold back a dissected arterial lining which can occlude the fluid passageway therethrough and to hold open a coronary artery after an angioplasty procedure.

Further details of prior art stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); and U.S. Pat. No. 4,886,062 (Wiktor), which are hereby incorporated herein in their entirety by reference thereto.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon to expand the stent into a permanent expanded condition and then deflating the balloon and removing the catheter.

Prior art stent designs provide a stent that is composed of wire mesh or weave having an open lattice structure or patterns. The open lattice structure of the prior art stents generally provide uniform strength along the center of the stent, but may be weak at the ends. This configuration may cause the prior art stents to be weaker at the stent ends because each portion at the ends has only one neighboring support portion. This inherent weakness at the ends of the prior art stents could result in the ends decreasing in diameter after implantation in a body lumen.

It may therefore be important to improve existing stent designs to provide stronger ends while allowing the centers to maintain the radial rigidity needed to hold open a body lumen while at the same time maintaining the longitudinal flexibility of the stent to facilitate its delivery into the blood vessel. The present invention satisfies these needs.

SUMMARY OF THE INVENTION

The present invention is directed to an expandable stent which is constructed to vary its structural strength along the length of the stent. This variation in structural strength along the length of the stent is accomplished in any one of several ways, including adjusting the wall thickness, varying the geometry of the open lattice or mesh pattern, or the temper of the material used. The strength of the stent can be designed to vary substantially or more gradually along the length of the stent. There can be configurations where it is advantageous to strengthen only one end of the stent. Such a stent would be useful for implantation in a tapered vessel where the one end of the stent is expanded to a larger diameter than the other end. This embodiment would also allow placement of the stent in ostial lesions where higher strength is needed at the ostial interface.

The stent of the present invention preferably includes an elongated tubular body having a first end section, a second end section, and a central section there between. The elongated tubular body will have an open lattice structure or weave that is adapted for radial expansion from the first, compressed diameter, to a second expanded diameter which approximates the inner diameter of the body lumen in which the stent is to be implanted.

In one embodiment of the invention, the first end section has a thicker open lattice structure than does the central section or the second end section, so that when the stent is expanded from its first, compressed diameter, to the second, enlarged diameter, the thicker open lattice structure on the first end section will be stronger and more resistant to crushing forces from recoil from the body lumen. The central section and the second end section will generally have a uniform structural thickness, which is less than the thicker open lattice structure of the first end section. In other embodiments, both the first end section and the second end section can have a thicker open lattice structure than the central section, so that the central section remains more flexible while the end sections are stronger and more resistant to radial crushing forces imposed by recoil of the body lumen.

In another embodiment of the invention, the first end section has an arcuate section with a thicker open lattice structure than does the central section or the second end section, so that when the stent is expanded from its first, compressed diameter, to the second, enlarged diameter, the arcuate section with the thicker open lattice structure of the first end section will be stronger and more resistant to crushing forces from recoil from the body lumen. An arcuate section of the stent is defined as a portion of the circumference of the stent when it is viewed from an end. Another way to define an arcuate section is to say that it is an arc of the outer surface of the stent when viewed from an end. In this embodiment, the remainder of the first end section, the central section and the second end section will generally have a uniform structural thickness, which is less than the arcuate section of the thicker open lattice structure of the first end section. In other embodiments, the entire stent lattice structure can have a thicker arcuate section of the open lattice structure than the remaining sections, so that the remaining sections remain more flexible while the thicker arcuate sections on the stent open lattice structure are stronger and more resistant to lateral crushing forces.

In one embodiment, the stent of the invention generally includes a plurality of radially expandable cylindrical elements which are relatively independent in their ability to expand and to flex relative to one another. The individual radially expanded cylindrical elements of the stent are dimensioned so as to be longitudinally shorter than their own diameters. Interconnecting elements or struts extending between adjacent cylindrical elements provide increased stability and are preferably positioned to prevent warping of the stent upon the expansion thereof. The resulting stent structure is an open lattice having a series of radially expandable cylindrical elements which are spaced longitudinally close enough so that small dissections in the wall of a body lumen may be pressed back into position against the lumen wall, but not so close as to compromise the longitudinal flexibility of the stent. The individual cylindrical elements cumulatively provide a stent which is flexible along its longitudinal axis, but which is stronger toward at least one end section to resist collapse in the areas where each portion of the stent has only one neighboring portion of pattern for cylindrical strength.

The stent embodying features of the invention can be readily delivered to the desired body lumen location by mounting it on an expandable member of a delivery catheter, for example, a balloon, and passing the catheter-stent assembly through the body lumen to the implant site. A variety of means for securing the stent to the expandable member on the catheter for delivery to the desired location are available. It is presently preferred to compress the stent onto the balloon. Other means to secure the stent to the balloon include providing a retractable sheath over the stent, ridges or collars on the inflatable member to restrain lateral movement of the stent, or using bioresorbable temporary adhesives to hold the stent on the balloon.

The presently preferred structure for the expandable cylindrical elements which form the stents of the present invention are generally circumferential undulating patterns, e.g., a generally serpentine pattern. The transverse cross-section of the undulating component of the cylindrical element is relatively small and preferably has an expansion ratio of about 1.0 to 4.5. The open reticulated structure of the stent allows for the perfusion of blood over a large portion of the arterial wall which can improve the healing and repair of a damaged arterial lining.

The cylindrical structures of the stent are plastically deformed when expanded (except with NiTi alloys) so that the stent will remain in the expanded condition and therefore they must be sufficiently rigid when expanded to prevent the collapse thereof in use. Furthermore, since at least one end section of the stent is formed of material that is thicker than the material of the stent nearer the center section, there is less chance of the end, or ends of the stent, collapsing after expansion and placement in the desired body lumen. During expansion of the preferred stent, portions of the undulating pattern will tip outwardly resulting in projecting members on the outer surface of the expanded stent. These projecting members tip radially outwardly from the outer surface of the stent and embed in the vessel wall and help secure the expanded stent so that it does not move once it is implanted.

When the stent is made from superelastic NiTi alloys, expansion occurs when the stress of compression is removed, thereby allowing the phase transformation from austenite back to martensite.

The elongated elements which interconnect adjacent cylindrical elements should have a transverse cross-section similar to the transverse dimensions of the undulating components of the expandable cylindrical elements to which they are attached. Thus, the first and second end sections of the stent are stronger because they have thicker material, and the elongated elements interconnecting those end sections should be correspondingly thicker, and thus correspondingly stronger than those elongated elements which interconnect adjacent cylindrical elements towards the center section of the stent.

Other features and advantages of the present invention will become more apparent from the following detailed description of the invention when taken in conjunction with the accompanying drawings.

BRIEF DESCRIPTION OF THE DRAWINGS

FIG. 6 is a schematic representation of laser equipment for selectively cutting tubing in the manufacturing of the stents of the present invention.

FIGS. 7 through 11 are perspective views schematically illustrating different stent configurations where both end sections of the stent have expandable elements that are made of thicker material than the central section.

FIG. 15 is a cross-sectional view depicting a stent configuration where the thickness of the cylindrical elements are substantially greater at each end of the stent than near the center of the stent.

FIG. 16 is a cross-sectional view depicting a stent configuration where the thickness of the cylindrical elements gradually increases from the center of the stent toward each end of the stent.

FIG. 17 is a cross-sectional view depicting a stent configuration where the thickness of the cylindrical elements substantially increases at one end only of the stent, and may extend for more than one element.

FIG. 18 is a cross-sectional view depicting a stent configuration where the thickness of the cylindrical elements gradually increase towards one end only of the stent.

DETAILED DESCRIPTION OF THE PREFERRED EMBODIMENTS

The stent of the present invention is generally delivered intraluminally using a conventional balloon catheter as is known in the art. The stent is used primarily to ensure the patency of the body lumen in which it is implanted. For example, the stent of the present invention preferably will be implanted in the coronary arteries after an angioplasty procedure to reinforce the artery against recoil or to tack up a dissection in the arterial wall. The stent of the present invention is useful for implanting in other body lumens, such as the carotid arteries, the illiacs, and other peripheral veins and arteries.

Figure 1:
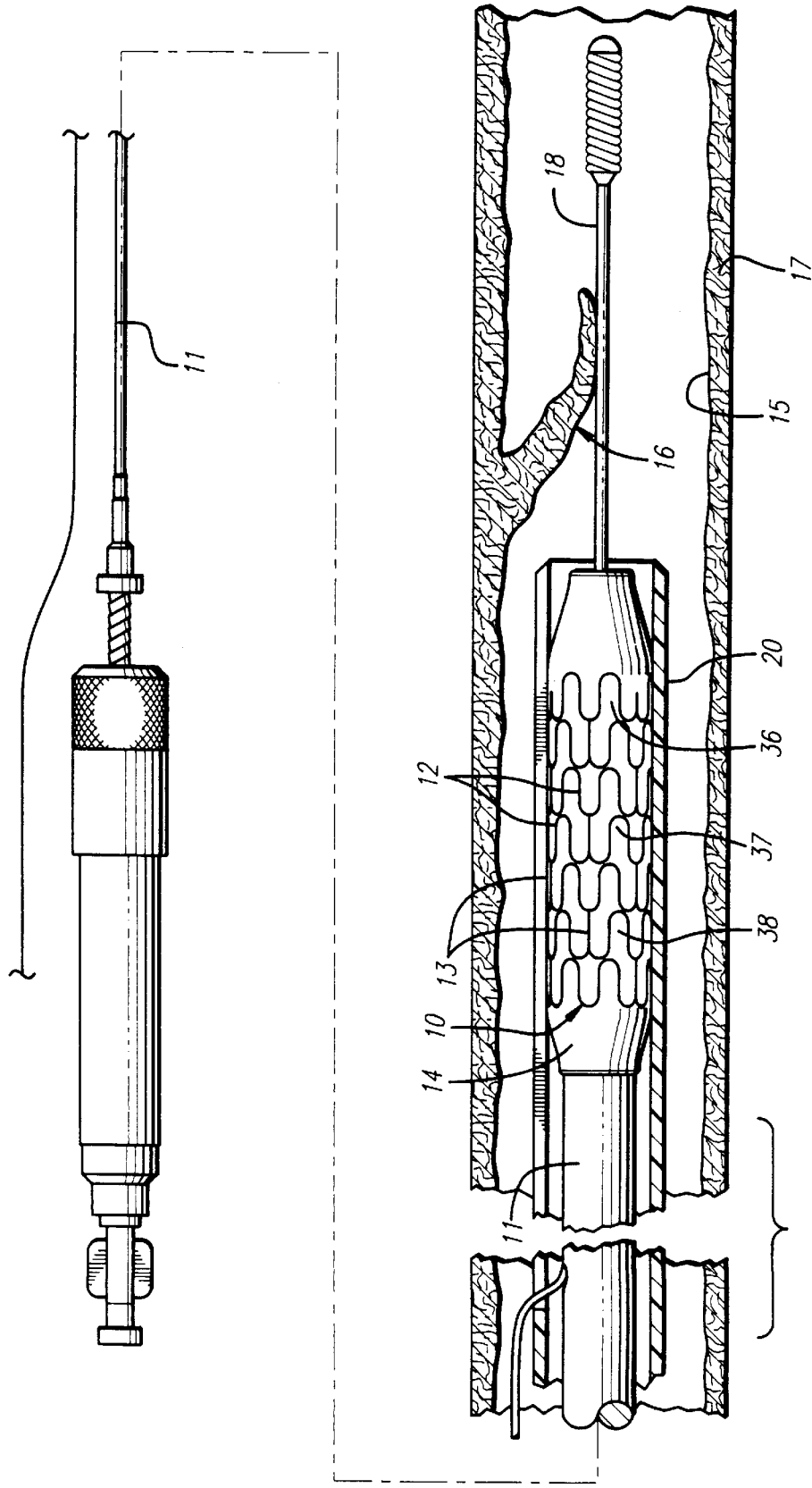
FIG. 1 is an elevational view, partially in section, of a stent embodying features of the invention which is mounted on a delivery catheter and disposed within an artery.

FIG. 1 illustrates stent 10, incorporating features of the invention, which is mounted on a delivery catheter 11. The stent preferably comprises a plurality of radially expandable cylindrical elements 12 disposed generally coaxially and interconnected by elements 13 disposed between adjacent cylindrical elements. The delivery catheter 11 has an expandable portion or balloon 14 for expanding the stent 10 within coronary artery 15. The artery 15, as shown in FIG. 1, has a dissected lining 16 which has occluded a portion of the arterial passageway. The ends of the stent have thicker elements which provide greater strength and resistance to collapse from recoil of the body lumen or artery 15.

The delivery catheter 11 onto which the stent 10 is mounted, is essentially the same as a conventional balloon dilatation catheter for anqioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used.

In order for the stent 10 to remain in place on the balloon 14 during delivery to the site of the damage within the artery 15, the stent 10 is compressed onto the balloon. A retractable protective delivery sleeve 20 may be provided to further ensure that the stent stays in place on the expandable portion of the delivery catheter 11 and prevent abrasion of the body lumen by the open surface of the stent 10 during delivery to the desired arterial location. Other means for securing the stent 10 onto the balloon 14 may also be used, such as providing collars or ridges on the ends of the working portion, i.e., the cylindrical portion, of the balloon.

Each radially expandable cylindrical element 12 of the stent 10 may be independently expanded. Therefore, the balloon 14 may be provided with an inflated shape other than cylindrical, e.g., tapered, to facilitate implantation of the stent 10 in a variety of body lumen shapes.

Figure 2:
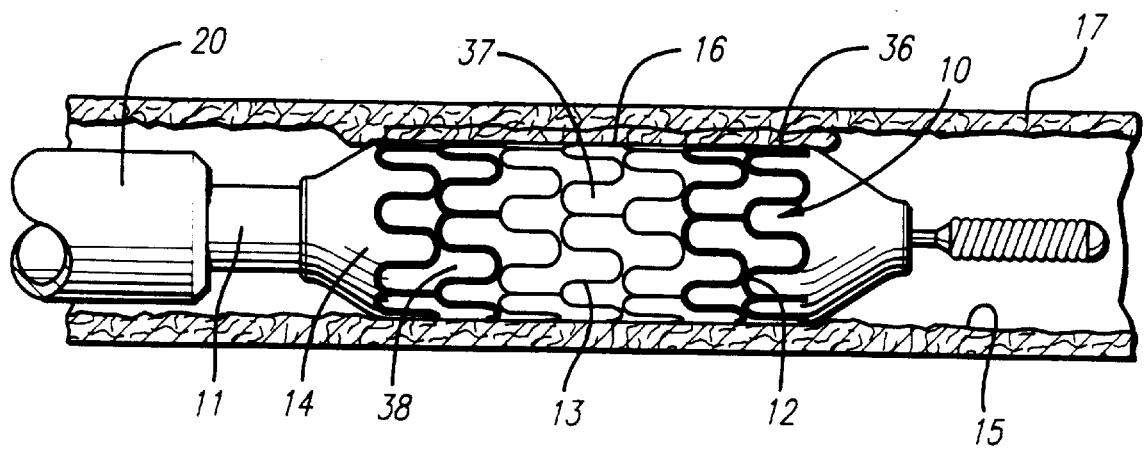
FIG. 2 is an elevational view, partially in section, similar to that shown in FIG. 1 wherein the stent is expanded within an artery, pressing the lining against the arterial wall.

The delivery of the stent 10 is accomplished in the following manner. The stent 10 is first mounted onto the inflatable balloon 14 on the distal extremity of the delivery catheter 11. The balloon 14 is slightly inflated to secure the stent 10 onto the exterior of the balloon. The catheter-stent assembly is introduced within the patient's vasculature in a conventional Seldinger technique through a guiding catheter (not shown). A guidewire 18 is disposed across a stenosed area or the damaged arterial section having a detached or dissected lining 16, and then the catheter-stent assembly is advanced over a guidewire 18 within the artery 15 until the stent 10 is directly under the detached lining 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of stenotic portions of an artery, the artery may have to be expanded in order to facilitate passage of blood or other fluid therethrough.

Figure 3:
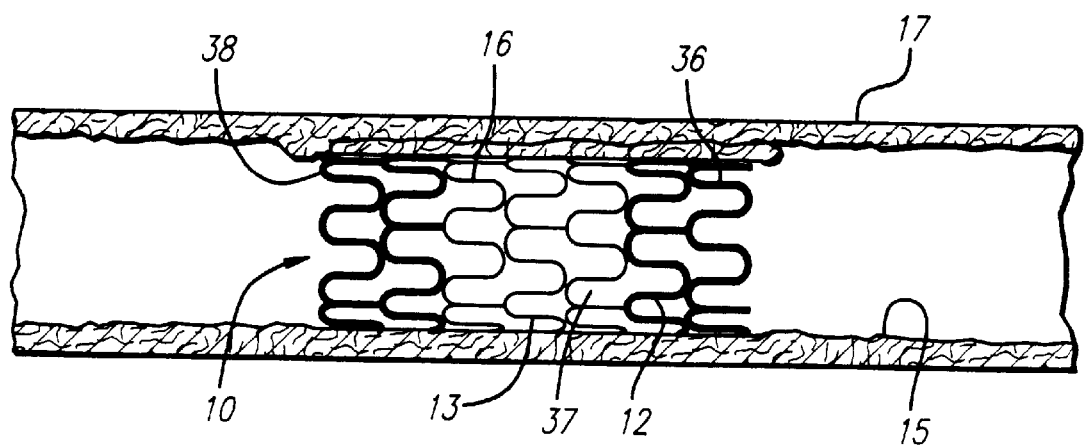
FIG. 3 is an elevational view, partially in section showing the expanded stent within the artery after withdrawal of the delivery catheter.

In a preferred embodiment, stent 10 serves to hold open the artery 15 after the catheter 11 is withdrawn, as illustrated by FIG. 3. Due to the formation of the stent 10 from elongated tubular member, the undulating component of the cylindrical elements of the stent 10 is relatively flat in transverse cross-section, so that when the stent is expanded, the cylindrical elements are pressed into the wall of the artery 15 and as a result do not interfere with the blood flow through the artery 15. The cylindrical elements 12 of stent 10 which are pressed into the wall of the artery 15 will eventually be covered with endothelial cell growth which further minimizes blood flow interference. The undulating portion of the cylindrical sections 12 provide good tacking characteristics to prevent stent movement within the artery. Furthermore, the closely spaced cylindrical elements 12 at regular intervals provide uniform support for the wall of the artery 15, and at least one end of the stent has expanded cylindrical elements that are stronger due to the material or design incorporated in the stent to prevent collapse of the stent at those locations in the body lumen. Consequently the stents of this invention are well adapted to hold open a body lumen or artery against recoil or to tack up and hold in place small flaps or dissections in the wall of the artery 15 as illustrated in FIGS. 2 and 3.

Figure 4:
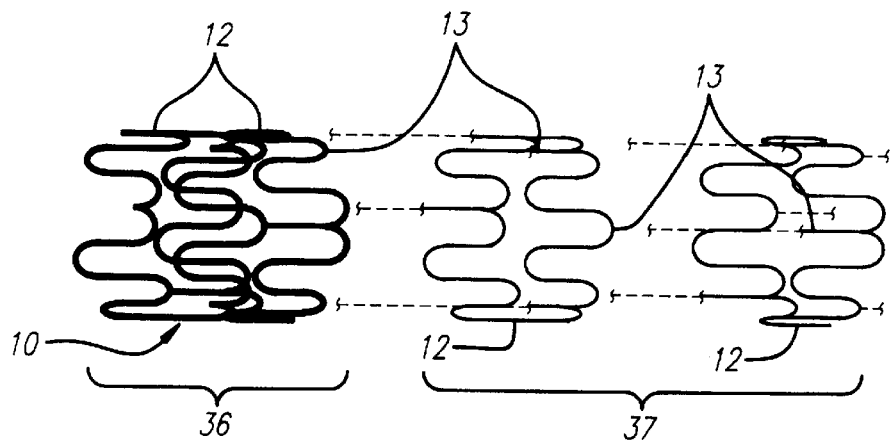
FIG. 4 is a perspective view of a stent embodying features of the invention in an unexpanded state, with one end of the stent being shown to illustrate one embodiment of the invention where thicker material is used to strengthen the end of the stent.

In a preferred embodiment of the invention, FIG. 4 depicts an enlarged perspective view of the stent 10 shown in FIG. 1, with first end section 36 of the stent having cylindrical elements 12 which are thicker from a material stand point than central section 37 to provide a stronger section at that location. First section 36 is stronger and more crush resistant due to arterial recoil than is central section 37 and second end section 38 (FIGS. 1–3) which do not have increased material thickness. FIG. 4 further shows the placement of interconnecting elements 13 between adjacent radially expandable cylindrical elements 12. Each pair of the interconnecting elements 13 on one side of a cylindrical element 12 are preferably placed to achieve maximum flexibility for a stent. In the embodiment shown in FIG. 4 the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions, yet is stronger at first end section 36.

Referring to FIGS. 7–11, alternate embodiments of stent 10 are depicted, wherein an open lattice structure 37 is in the form of a tubular member. Each stent is capable of being expanded from a first, compressed diameter to a second enlarged diameter within a body lumen, such as artery 15 as depicted in FIGS. 1–3. Thus, as with the embodiment of the stent of FIG. 4, the embodiment of the stents depicted in FIGS. 7–11 are expandable and will deform beyond their elastic limit to maintain the patency of the body lumen or artery 15. As depicted, the embodiment shown in FIGS. 7–11 have a first section 36 and second section 38 which are of thicker material than is central section 37. The first and second sections 36,38 are stronger and more resistant to recoil of the artery 15, and help secure stent 10 within the artery. As described herein, the stents of FIGS. 7–11 can have either the first end section 36 of thicker material, or both the first and second sections 36,38 having thicker material. Further, the material may become thicker in a tapered manner as described for FIGS. 16–18.

A preferred configuration for stent 10 is depicted in FIGS. 4 and 12–14, where cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32, and Y-shaped members 33, each having varying radii of curvature so that expansion forces are more evenly distributed over the various members.

Figure 13:
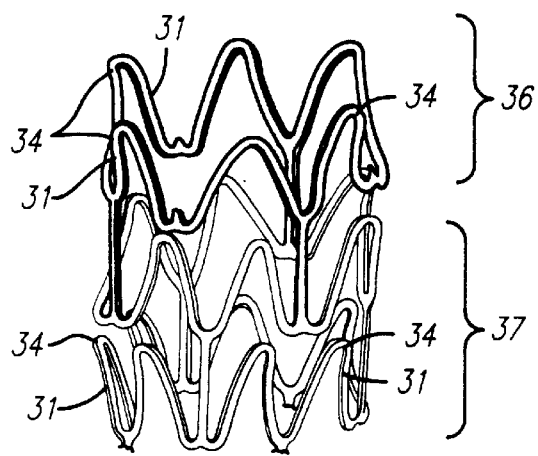
FIG. 13 is a perspective view of a non-end portion of the stent of FIG. 4 after it is fully expanded depicting some members projecting radially outwardly.
Figure 14:
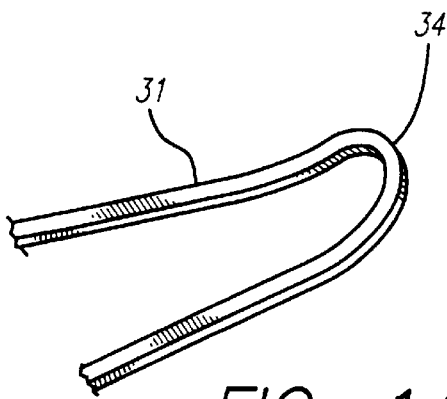
FIG. 14 is an enlarged, partial perspective view of one U-shaped member with its tip projecting outwardly after expansion.

As depicted in FIGS. 13 and 14, after cylindrical elements 12 have been radially expanded, outwardly projecting edges 34 are formed. That is, during radial expansion U-shaped members 31 will tip outwardly thereby forming outwardly projecting edges. These outwardly projecting edges provide for a roughened outer wall surface of stent 10 and assist in implanting the stent in the arterial wall by embedding into the arterial wall. In other words, outwardly projecting edges embed into the arterial wall, for example artery 15, as depicted in FIG. 3. Depending upon the dimensions of stent 10 and the thickness of the various members making up the serpentine pattern 30, any of the U-shaped members 31, W-shaped members 32, and Y-shaped members 33 can tip radially outwardly to form a projecting edge 34. It is most likely and preferred that U-shaped members 31 tip outwardly since they do not join with any connecting member 13 to prevent them from expanding outwardly. As can be seen in FIG. 13, first end section 36 has thicker U, W and Y shaped members than does central section 37. The thicker members at first end section 36 will provide substantially more support and resist crushing due to recoil from artery 15 than will central section 37. Likewise, when both end sections 36, 38, as depicted in FIGS. 15–16 are thicker, they provide substantially more support in artery 15, and securely embed in artery 15 due to the projecting edges 34 tipping outwardly.

FIGS. 15 through 18 schematically depict various preferred embodiments of stents of the invention. One such configuration provides a stent where the thickness, and thus strength, of the expandable cylindrical elements 12 substantially increase at first and second end sections 36, 38 of the stent 10, as shown in FIG. 15. In another embodiment, the expandable cylindrical elements 12 gradually increase in thickness toward first and second end sections 36, 38, and thus strength, moving axially from the center section 37 of the stent toward either end, as shown in FIG. 16. In another embodiment shown in FIG. 17, the thickness of the expandable cylindrical elements 12 substantially increase at first end section 36 of stent 10. Increased thickness at end 36 only of stent 10, could occur gradually as depicted in FIG. 18.

Figure 19:
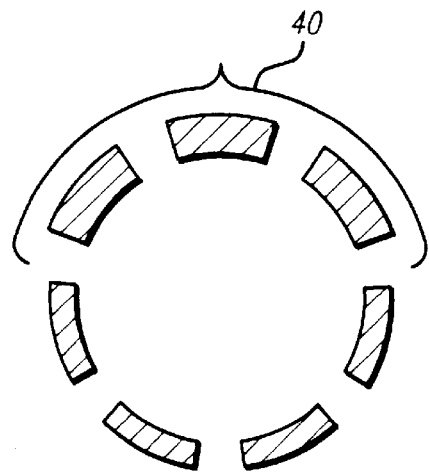
FIG. 19 is an end view depicting a stent configuration where the thickness of an arcuate section of the open lattice structure of the stent is substantially thicker than the adjacent arcuate section.

FIG. 19 schematically depicts another preferred embodiment of the stent of the invention, where the thickness, and thus strength, of the expandable cylindrical elements 12 substantially increase at arcuate section 40 of the open lattice structure of the stent 10. The thicker arcuate section 40 can be limited to a portion of first end section 36 or the entire first end section, or it can extend longitudinally to a plurality of sections, even to the entire length of the stent.

In the preferred embodiment, stent 10 is formed from a metal alloy tube such as stainless steel tubing, however, it can be made from other metal alloys including, but not limited to, tantalum, NiTi, or from thermoplastic polymers. Presently, a preferred mode of making the stent is by direct laser cutting a stainless steel tube as described in commonly owned U.S. Pat. No. 5,780,807, filed Nov. 28, 1994, entitled METHOD AND APPARATUS FOR DIRECT LASER CUTTING OF METAL STENTS, which is incorporated herein in its entirety by reference. Other modes of making the stent of the invention are also contemplated.

While the invention has been illustrated and described herein in terms of its use as an intravascular stent in the coronary arteries, it is envisioned that the stent will be useful in other body lumens as well. Due to the high strength characteristics of the stent of the present invention, primarily due to the thicker wall elements at the ends of the stent, it is particularly adapted for use in the coronary arteries, for anchoring a graft for repairing an aortic aneurysm, and for peripheral veins and arteries throughout the body. Other modifications and improvements can be made to the invention without departing from the scope thereof.

What is claimed is:

1. An intravascular stent for implanting in a body lumen, comprising;

a single walled tubular body of a biocompatible material having a first end section, a second end section, and a central section, each said section being defined by the thickness of the material making up the wall of the tubular body;

said tubular body further having an open lattice structure formed from a single piece of metal alloy and adapted for radial expansion from a first compressed diameter, to an enlarged, second diameter; and said first end section wall thickness being greater than said central section wall thickness and said second end section wall thickness, so that when said stent is expanded to said enlarged, second diameter, said first end section is radially stronger and more crush resistant than said central section or said second end section.

2. The stent of claim 1, wherein both said first end section and said second end section have a wall thickness greater than said central section wall thickness, making said first end section and said second end section substantially radially stronger than said central section.

\* \* \* \* \*

UNITED STATES PATENT AND TRADEMARK OFFICE
CERTIFICATE OF CORRECTION

Figure 5:
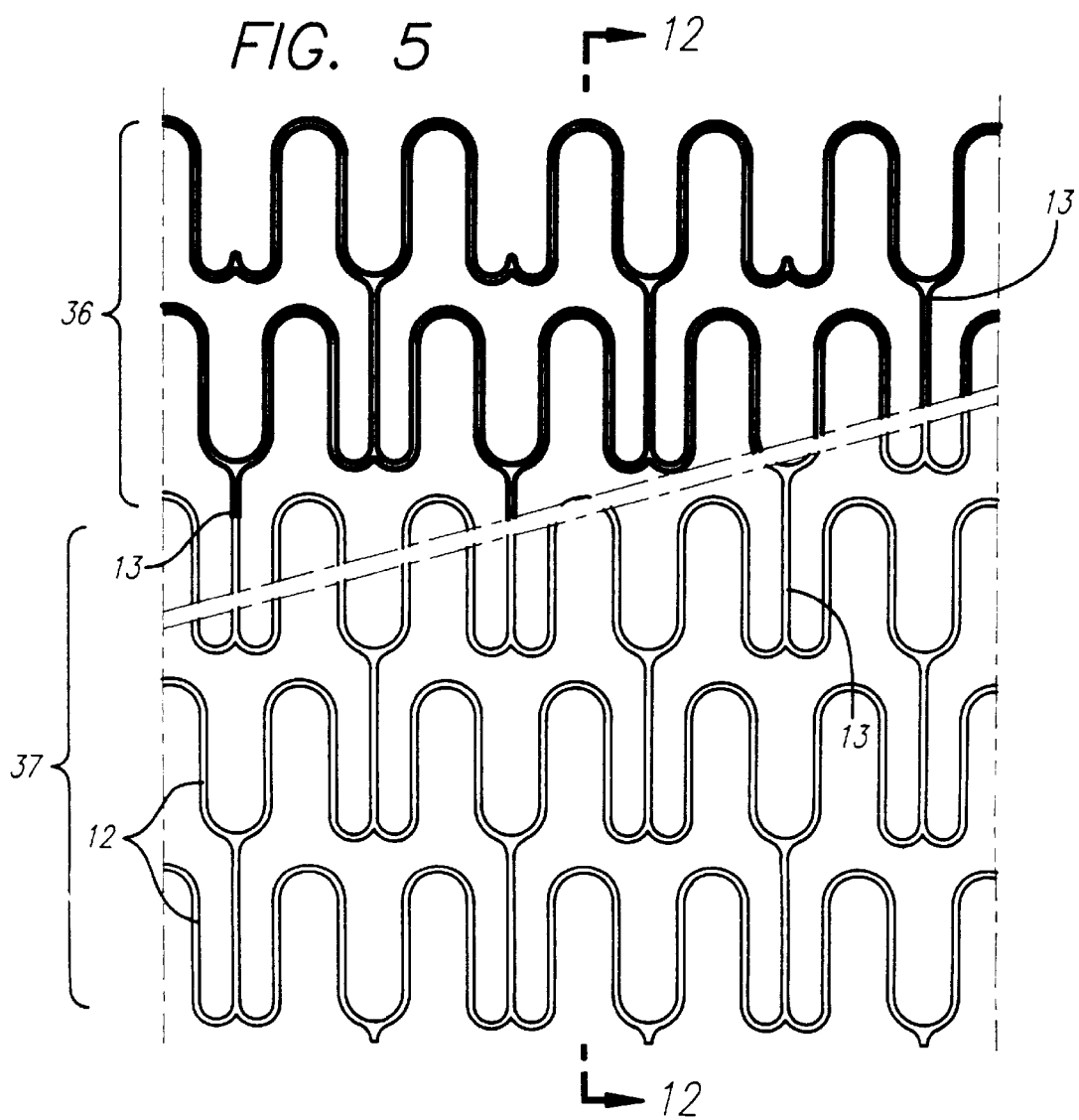
FIG. 5 is a plan view of a flattened section of a stent of the invention which illustrates the undulating pattern of the stent shown in FIG. 4 and identifies one embodiment of the invention where one end of the stent is made of thicker material for added strength.
Figure 9:
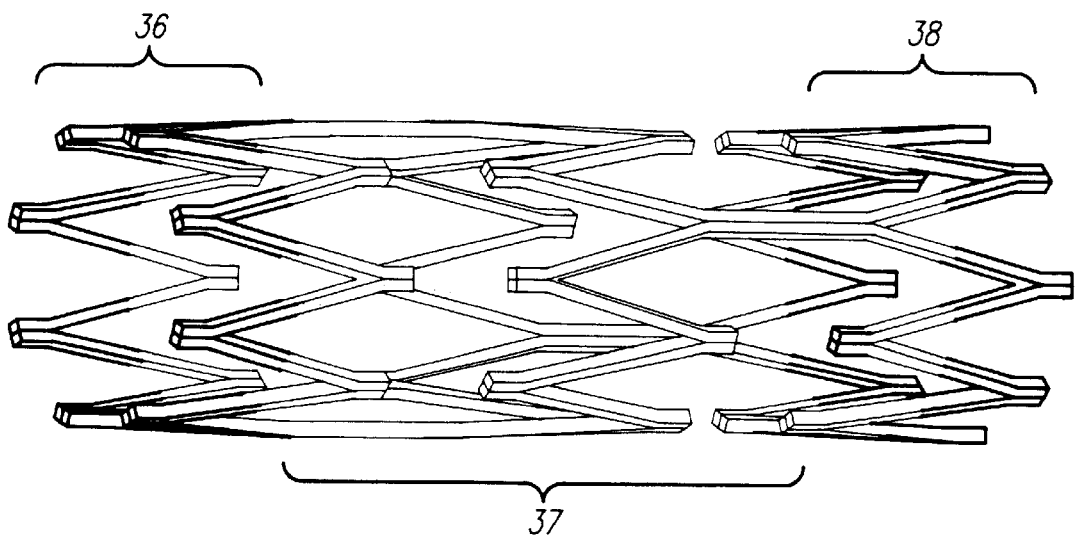
Figure 10:
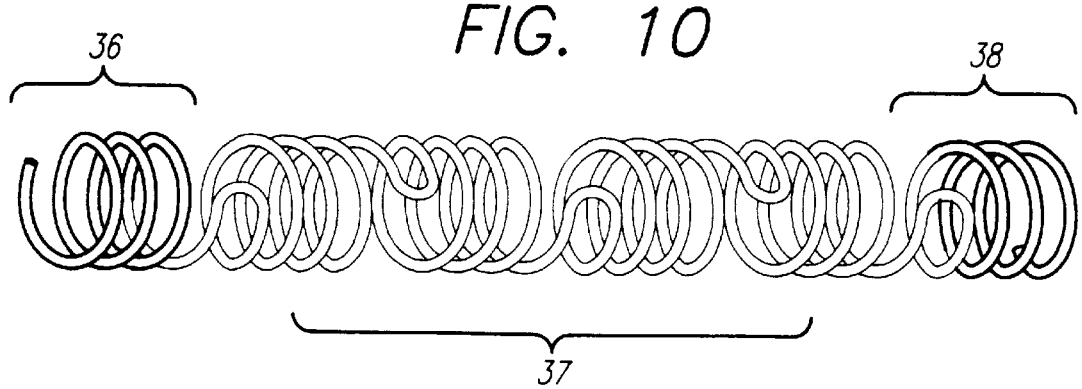
Figure 11:
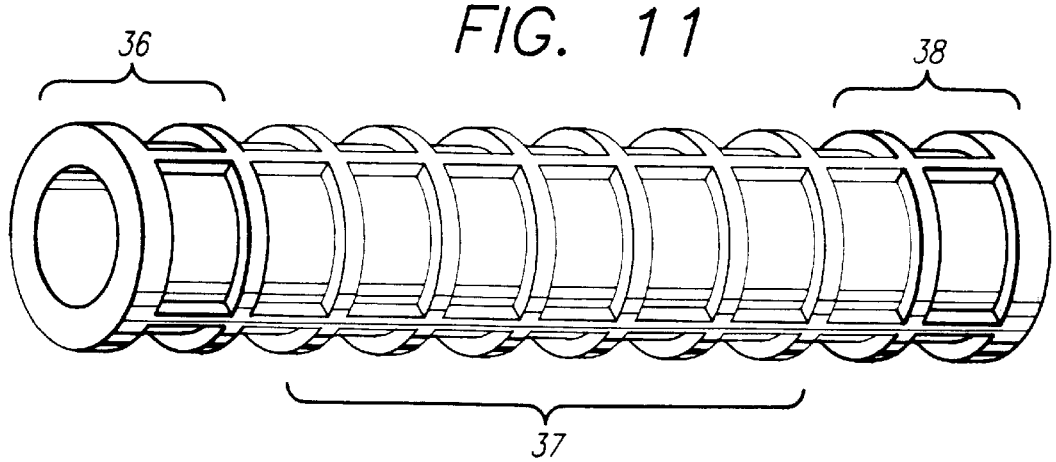
Figure 12:
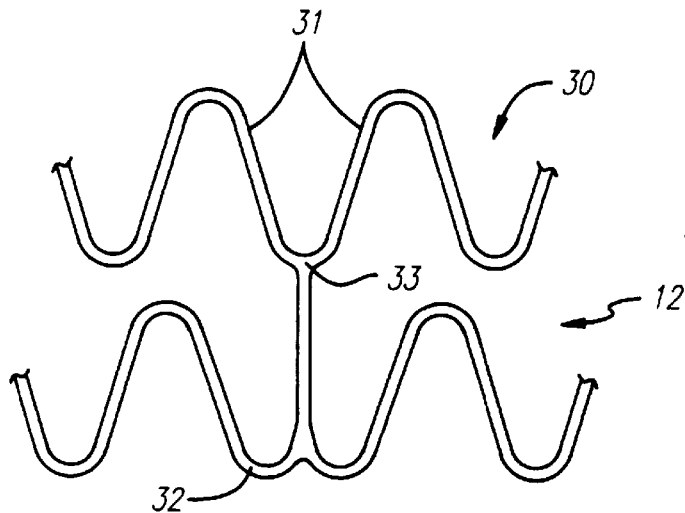
FIG. 12 is an enlarged partial view of the stent of FIG. 5 with the various, non-end members slightly expanded.

PATENT NO.  : 6,027,526
DATED       : Feb. 22, 2000
INVENTOR(S) : Timothy A. Limon, Todd H. Turnlund It is certified that error appears in the above-identified patent and that said Letters Patent is hereby corrected as shown below:

Column 4, line 25, after "FIG.5, add --taken along lines 12-12--.

Column 6, line 36, after "36.", add --FIG.5 illustrates the stent of FIG.4 in a flattened condition to more clearly depict the undulating pattern and the cross section of certain portions of the stent.--.

Column 8, line 32, claim 1, change "a dapted", to read --adapted--.

Signed and Sealed this

First Day of May, 2001

Attest:

NICHOLAS P. GODICI

Attesting Officer        Acting Director of the United States Patent and Trademark Office